(12) United States Patent
Berlepsch et al.

(10) Patent No.: US 9,468,778 B2
(45) Date of Patent: Oct. 18, 2016

(54) HAIR TREATMENT METHOD, KIT, RECIPIENT, AND USE THEREOF

(71) Applicant: The Procter & Gamble Company, Cincinnati, OH (US)

(72) Inventors: Joseph Allen Berlepsch, Hamilton, OH (US); Jaime Beverly Stahl, Loveland, OH (US); James Douglas Still, Cleves, OH (US); Lucio Frias, Cincinnati, OH (US); Robert Drennan Lewis, West Chester, OH (US); Leobaldo Antonio Perdomo, Milford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/465,478

(22) Filed: Aug. 21, 2014

(65) Prior Publication Data

US 2015/0059793 A1    Mar. 5, 2015

Related U.S. Application Data (60) Provisional application No. 61/870,284, filed on Aug. 27, 2013.

(51) Int. Cl.
| | |
|---|---|
| *A61Q 5/10* | (2006.01) |
| *A45D 7/04* | (2006.01) |
| *A45D 19/00* | (2006.01) |
| *A45D 19/06* | (2006.01) |
| *A61Q 5/04* | (2006.01) |
| *B65D 25/04* | (2006.01) |
| *A61Q 5/00* | (2006.01) |
| *A45D 7/00* | (2006.01) |

(52) U.S. Cl.
CPC . *A61Q 5/10* (2013.01); *A45D 7/04* (2013.01); *A45D 19/0008* (2013.01); *A45D 19/06* (2013.01); *A61Q 5/00* (2013.01); *A61Q 5/04* (2013.01); *B65D 25/04* (2013.01); *A45D 2007/002* (2013.01); *A45D 2019/0066* (2013.01); *A61K 2800/87* (2013.01); *A61K 2800/88* (2013.01)

(58) Field of Classification Search
CPC ............. A45D 19/06; A45D 19/00; A45D 2019/0066; A45D 19/02; A45D 2200/25; A45D 27/22; A45D 2007/001; A61Q 5/10; A61Q 5/08; A61Q 5/065; A61Q 5/06
USPC .................. 132/200, 208, 209, 270; 206/581
See application file for complete search history.

(56) References Cited

U.S. PATENT DOCUMENTS

| | | | |
|---|---|---|---|
| D117,898 S | * | 12/1939 | Carawan ........................ D28/20 |
| 2,528,378 A | | 10/1950 | Mannheimer |
| 2,781,354 A | | 2/1957 | Mannheimer |

(Continued)

FOREIGN PATENT DOCUMENTS

| | | |
|---|---|---|
| FR | 2953397 B1 | 1/2012 |
| JP | 08333224 A | 12/1996 |
| JP | 2010248103 A | 11/2010 |

*Primary Examiner* — Robyn Doan
(74) *Attorney, Agent, or Firm* — James T. Fondriest (57) ABSTRACT

A method of treating hair, a hair treatment kit for extemporaneous preparation of hair treatment compositions, a recipient for applying hair treatment compositions, and use thereof are provided. The invention provides a superior hair treatment performance such as a superior hair coloring and/or bleaching performance, particularly for providing superior root to tip treatment evenness.

18 Claims, 2 Drawing Sheets

(56) References Cited

U.S. PATENT DOCUMENTS

| | | | | |
|---|---|---|---|---|
| 5,458,087 A | * | 10/1995 | Prior et al. | 119/51.5 |
| 6,099,828 A | | 8/2000 | Kajino | |
| 6,666,045 B1 | * | 12/2003 | Song | F25D 23/003 62/441 |
| 6,835,018 B2 | | 12/2004 | Miczewski | |
| 7,389,892 B2 | * | 6/2008 | Park | 220/697 |
| 7,407,055 B2 | * | 8/2008 | Rodriguez | 206/581 |
| 7,472,595 B2 | * | 1/2009 | Ploix | 73/426 |
| 7,875,269 B2 | | 1/2011 | Bureiko | |
| 8,632,611 B2 | | 1/2014 | Agostino | |
| 2003/0008855 A1 | * | 1/2003 | Simon | A61K 8/23 514/184 |
| 2006/0231115 A1 | * | 10/2006 | McNamara | 132/208 |
| 2008/0178399 A1 | | 7/2008 | Franco | |
| 2010/0154816 A1 | * | 6/2010 | Goddard-Clark et al. | 132/208 |
| 2010/0200012 A1 | * | 8/2010 | Sloan | 132/200 |
| 2011/0114107 A1 | * | 5/2011 | Muhl et al. | 132/200 |
| 2013/0089587 A1 | * | 4/2013 | Staudigel | A61Q 5/12 424/401 |
| 2013/0220358 A1 | * | 8/2013 | Agostino et al. | 132/208 |
| 2015/0053231 A1 | * | 2/2015 | Bonauer et al. | 132/208 |
| 2015/0053232 A1 | * | 2/2015 | Schofield | 132/208 |

* cited by examiner

HAIR TREATMENT METHOD, KIT, RECIPIENT, AND USE THEREOF

FIELD OF THE INVENTION

The invention relates to a method of treating hair, a hair treatment kit for extemporaneous preparation of hair treatment compositions, a recipient for applying hair treatment compositions, and use thereof. The invention provides a superior hair treatment performance such as a superior hair colouring and/or bleaching performance, particularly for providing superior root to tip treatment evenness.

BACKGROUND OF THE INVENTION

For consumers who have previously coloured their hair, the colour and condition of the hair is not homogenous along the entire length. The hair strands will comprise root virgin hair or new growth hair which has not been previously coloured and conversely at the tips hair which has experienced one or multiple hair colouring treatments. The tips of the hair typically are the most damaged portion of the hair and the colour will have changed over time dependant on the wash fade profile and number of types of hair colourant applied, amongst many relevant factors. The intermediate hair length is typically a medium between these two extreme conditions. As a consequence in the salon, for consumers who have previously coloured their hair, the salon stylists typically will colour the root virgin hair first with a specific composition to most effectively colour the hair to the desired end result. However, the remaining length of the hair and tips which has been previously coloured and may have undergone multiple colouring cycles is coloured with a separate and different composition to that applied at the roots. In this manner the salon stylist aims to provide a homogenous end colour result along the entire length of hair from root to tip independent of the variations of starting hair colour and condition along the hair length. Such method requires advanced professional skills in colouring hair for ensuring that the end result is satisfactory. Most consumers do not master such skills, and are unable to treat different strands and/or portions of hair with different hair colourant for achieving a satisfactory blend of tones.

The need for providing a retail hair treatment system, particularly a retail hair colouring and/or bleaching system, for use on roots and the entire hair length, has been met with the hair colouring methods, kits and compositions thereof disclosed in PCT patent application PCT/U.S.2013/027268, filed on 22 Feb. 2013. In such method, it is provided a first composition being a non-diluted hair colouring composition, and a dilutant component. A first portion of the first composition is applied onto hair, preferably onto hair roots, while the remaining second portion is mixed with the dilutant component for obtaining a diluted hair colouring composition, which is then applied onto hair, preferably onto hair lengths and tips. Alternative methods, compositions and kits have also been considered. For example, the first composition may be a hair perming composition and/or the second composition may a hair colouring and/or bleaching composition, a hair perming composition, a dilutant composition, a composition of lower pH than the first composition, a composition of higher pH than the first composition.

These methods, kits and compositions have proven useful for achieving a satisfactory hair treatment performance such as a superior hair colouring and/or bleaching performance, particularly for providing satisfactory root to tip treatment evenness. However, some consumers still struggle, after having applied the first portion of the first composition onto hair, in properly mixing the second portion with the second composition in the appropriate proportions and/or in a homogeneous fashion. Even when clear and detailed instructions have been provided, some consumers still find it difficult to obtain the mixed composition. Inappropriate and/or inhomogeneous mixing may provide, after application of the hair colouring composition onto hair, to unsatisfactory results such as differing and/or inhomogeneous tones, inappropriate blend of tone.

There is the need therefore for providing an improved method for treating hair being easy and intuitive to put into practise, even for the non-trained user. There is also the need for providing a method of treating hair for consumers having limited experience and/or skills in treating hair such hair colouring and/or bleaching hair.

SUMMARY OF THE INVENTION

In one aspect, the present invention relates to a method for treating hair comprising the steps of: providing a first composition having a viscosity of from about 20 to about 200 Pa at 10 s$^{-1}$; providing a second composition, wherein said composition is compatible for mixing with the first composition; providing a recipient comprising a base, a frame attached circumferentially to the base, and a cavity delimitated by the base and the frame and being suitable for containing a hair treatment composition, wherein the frame comprises a partition means and/or indicia for physically or virtually splitting the volume of the cavity into at least two adjacent sub-volumes; pouring the first composition into the cavity of the recipient; applying a first portion of the first composition onto the hair; retaining a second portion of the non-applied first composition, the volume of said second portion corresponding to one of the two sub-volumes of the cavity; pouring the second composition into the other sub-volume; mixing the second composition with the non-applied first composition; applying the mixed composition to the hair. In a preferred aspect, the first portion of the first composition is applied onto the hair roots and the composition obtained by mixing the second composition with the second portion of the first composition is applied onto the hair lengths and tips.

In another aspect, the present invention relates to a hair treatment kit, for extemporaneous preparation of hair treatment compositions, comprising a first composition, a second composition and a recipient as abovementioned.

In another aspect, the present invention relates to a recipient suitable for containing hair treatment compositions comprising: a base; a frame attached circumferentially to the base, and a cavity delimitated by the base and the frame and being suitable for containing hair treatment compositions; wherein the frame comprises a partition means and/or indicia for virtually or physically splitting the volume of cavity into at least two adjacent sub-volumes.

In another aspect, the present invention relates to the use of a recipient as abovementioned as a support for containing two differing hair treatment compositions, before their application onto different portions of hair, preferably before their respective application on the roots and lengths/tips of hair.

DETAILED DESCRIPTION OF THE INVENTION

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention. The terms "root", "hair roots", "root hair line" and "virgin hair" all refer to hair which has not been previously treated with a hair colouring composition.

In some specific embodiments of the present invention, the hair colouring and/or bleaching compositions are applied to hair which has already been previously coloured with hair colouring compositions. In such a case, the terms "root", "hair roots", "root hair line" and "virgin hair" all refer to the portion of hair having grown, since the last hair colouration, said portion of hair being virgin, i.e. naturally-coloured and the terms "hair lengths and tips" refer to the remaining portion of hair having been already previously coloured.

By "hair colouring" composition it is meant a composition suitable for changing the colour of hair. The hair colouring composition is referred hereinafter as "the composition", unless otherwise specified. The hair colouring composition can comprise oxidative dye precursors, direct dyes or even no, or substantially no, dyes in case of bleaching only compositions where the change of colour is mainly caused by the degradation of the natural melanin contained in the hair shaft by the oxidizing agent. The term "hair colouring" composition as used herein covers hair bleaching and hair oxidative dyeing products.

All percentages are by weight of the hair colouring composition, i.e. of the ready-to-use composition, unless otherwise specified. When more than one composition are used during a treatment, the total weight to be considered is the total weight of all the compositions applied on the hair simultaneously (i.e. the weight found "on head"), typically resulting from mixing an oxidative composition (also called developer and/or oxidizing composition/component) with a dye composition (also called tint, and/or dye composition/component), unless otherwise specified. All ratios or percentages are weight ratios or weight percentages unless specifically stated otherwise.

The inventors have surprisingly found that, by designing a specific recipient 1 and by selecting a first composition having a defined viscosity, it could be provided an improved method for treating hair being easy and intuitive to put into practice, particularly for the non-trained user. Such method allows obtaining a superior hair treating performance such as hair colouring and/or bleaching performance, particularly for providing superior root to tip treatment evenness and/or for providing superior blend of tones. Indeed, the inventors have found that providing a recipient 1 comprising a partition means and/or indicia together with a first composition having a viscosity of sufficient value for not flowing freely is of advantage for helping the user using the right amount of the first portion of the first composition to be applied onto hair and therefore retaining the right amount of a second portion of the first composition 3 for subsequent mixing with the second composition. This has proven superior to conventional methods, where the first composition is poured into a conventional recipient deprived of any partition means and/or indicia, and after applying a first portion of it onto hair and retaining a second portion of it, and where the second composition is merely poured on top of said second portion. Such conventional methods are not practical, in that the user could hardly know whether s/he has retained the right amount of the first composition. In contrast, by providing a first composition which is viscous enough so that it does not flow freely, the user could easily and intuitively retain and then push and/or pack the right amount of the non-applied portion 3 of the first composition, thanks to the partition means and/or indicia 13 helping identifying easily and intuitively what the amount should be, as correlated to one sub-volume of the recipient 1.

The First Composition

The method for treating hair according to the invention comprises the step of providing a first composition having a viscosity of from about 20 to about 200 Pa at $10\ s^{-1}$, or from about 30 to about 200 Pa at $10\ s^{-1}$, or from about 100 to about 200 Pa at $10\ s^{-1}$, from about 130 to about 180 Pa at $10\ s^{-1}$, as measured according to the viscosity test method (step i). Providing a first composition having such viscosity is essential for ensuring that the composition does not flow freely, particularly does not flow freely within 60 min, or within 40 min, or within 30 min, or within 20 min. So that, after applying a first portion of it onto hair, the remaining second portion 3 can be pushed and/or packed on one side of the recipient 1 into the sub-volume delimitated by the partition means and/or indicia 13. In addition, such viscosity enables the first portion of the first composition to be applied directly to the roots without any dripping or running down the hair lengths and also enables the mixed composition (see step xi) to be easily applied and distributed along the entire remaining hair length with minimal to no dripping from the hair.

The first composition may be selected from the group consisting of a hair colouring and/or bleaching hair, a hair perming composition, and mixtures thereof; or a hair colouring and/or bleaching composition; or a hair colouring composition comprising a dye compound; or a hair colouring composition comprising a dye compound selected from the group consisting of an oxidative dye precursor, a direct dye compound, and mixtures thereof; or an oxidative hair colouring composition comprising an oxidative dye precursor and optionally a direct dye compound.

Whenever the first composition is an oxidative hair colouring composition, it may be obtained by: providing a developer component comprising an oxidizing agent; providing a dye component comprising an oxidative dye precursor and/or an alkalizing agent; optionally pouring, sequentially or simultaneously, the developer and the dye components into the cavity of the recipient; mixing the developer component and the dye component homogenously; preferably at a mixing ratio of from about 1:5 to about 5:1, or at a ratio of from about 1:2 to about 2:1, or at a ratio of about 1:1.

The first composition may comprise a solvent. Any suitable solvent known in the art may be used. For example, the solvent may be selected from the group consisting of water, ethanol, propanol, isopropanol, glycerol, 1,2-propylene glycol, hexylene glycol, ethoxy diglycol, and mixtures thereof; and/or it may be present in a total amount ranging from at least about 50% by total weight of the first composition.

The first composition, and the developer component, may comprise source of an oxidizing agent. Any suitable oxidizing agent known in the art may be used. For example, the oxidizing agent may be selected from the group consisting of hydrogen peroxide, percarbonates, persulphates, and mixtures thereof; and/or it may be present in a total amount ranging from about 0.1% to about 10% by total weight of the first composition.

The first composition, and the dye component, may comprise an alkalizing agent. Any suitable alkalizing agent known in the art may be used. For example, the alkalizing agent may be selected from the group consisting of ammonia, ammonium salts including ammonium carbonates, non-ammonia alkalizing agents including monoethanolamine; and/or it may be present in a total amount of from about 0.1% to about 10% by total weight of the first composition.

The first composition, and the dye component, may comprise an oxidative dye precursor, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof. For example, the oxidative dye precursor may be present in a total amount of up to about 12% by total weight of the first composition. Suitable primary intermediates include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, salts thereof and mixtures thereof. Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

The first composition, and the dye component, may comprise a direct dye. For example, the direct dye may be present in a total amount of from about 0.05% to about 4% by total weight of the first composition. Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No.2, HC Yellow No. 4, HC Yellow No. 2, HC Orange No. 1, HC Red No. 1,2-(4-amino-2-chloro-5-nitrophenylamino)ethanol, HC Red No. 3,4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No.1, HC Blue No. 14; Natural dyes such as Annato, Anthocyanin, Beetroot, Carotene, Capsanthin, Lycopene, Chlorophyll, Henna, Indigo, Cochineal; and mixtures thereof.

The first composition, and any of the dye and/or the developer component(s), may comprise a chelant (also known as "chelating agent", "sequestering agent", or "sequestrant") in an amount sufficient to reduce the amount of metals available to interact with formulation components, particularly oxidizing agents, more particularly peroxides. Any suitable chelants known in the art may be used. For example, the chelant may be selected from the group consisting in carboxylic acids, phosphonic acids, polyphosphoric acids, their salts thereof, and mixtures thereof; or from the group consisting of DTPA, DTPMP, EDDS, their salts thereof, their derivatives thereof, and mixtures thereof; or EDDS. For example, the chelant may be present in a total amount of at least about 0.01% by total weight of the first composition.

The composition may comprise a radical scavenger. As used herein the term "radical scavenger" refers to a species that can react with a radical, preferably a carbonate radical to convert the radical species by a series of fast reactions to a less reactive species. For example, the radical scavenger may be selected from the group consisting of glycine, sarcosine, lysine, serine, 2 methoxyethylamine, glucosamine, glutamic acid, morpholine, piperdine, ethylamine, 3 amino-1-propanol, and mixtures thereof; and/or it may present in a total amount of from about 0.1% to about 10% by total weight of the first composition.

The first composition may comprise a pH modifier and/or buffering agent in an amount that is sufficiently effective to adjust the pH of the composition to fall within a range from about 3 to about 13, alternatively from about 8 to about 12, alternatively from about 9 to about 11.

The first composition may comprise a thickener in an amount sufficient to provide the composition with a viscosity so that it can be readily applied to the hair without unduly dripping off the hair and causing mess. For example, the thickener may be selected from the group consisting of associative polymers, polysaccharides, non-associative polycarboxylic polymers, and mixtures thereof; and/or it may be present in a total amount of from at least about 0.1% by total weight of the first composition.

The first composition may comprise a source of carbonate ions, carbamate ions, hydrogen carbonate ions, and mixtures thereof in a sufficient amount to reduce damage to the hair during the colouring process. For example, the source of carbonate ions may be selected from the group consisting of ammonium carbonate, ammonium hydrogen carbonate, and mixtures thereof; and/or it may be present in a total amount of from about 0.1% to about 15% by total weight of the first composition.

The first composition may comprise a conditioning agent. Any suitable conditioning agent known in the art may be used. For example, the conditioning agent may be selected from the group consisting of silicones, aminosilicones, fatty alcohols, polymeric resins, polyol carboxylic acid esters, cationic polymers, cationic surfactants, insoluble oils and oil derived materials and mixtures thereof; and/or it may be present in a total amount of from about 0.05% to about 20% by total weight of the first composition.

The first composition may comprise a surfactant. Any suitable surfactant known in the art may be used. For example, the surfactant may be selected from the group consisting of surfactants generally having a lipophilic chain length of from about 8 to about 30 carbon atoms and being selected from anionic surfactants, nonionic surfactants, amphoteric surfactants, cationic surfactants, and mixtures thereof; and/or it may be present in a total amount of from about 1% to about 60% by total weight of the first composition.

The first composition may comprise, in addition to the ingredients indicated above, further ingredients in order to further enhance the properties of the composition, as long as these are not excluded by the claims. Suitable further ingredients include, but not limited to: fragrances; enzymes; dispersing agents; peroxide stabilizing agents; antioxidants; natural ingredients (such as proteins, protein compounds, and plant extracts); ceramides; preserving agents; opacifiers and pearling agents (such as titanium dioxide and mica); and mixtures thereof.

The Second Composition

The method also comprises the step of providing a second composition, wherein said composition is compatible for mixing with the first composition (step ii). The second composition may be selected from the group consisting of a hair colouring and/or bleaching composition, a hair perming composition, a dilutant composition, a composition of lower pH than the first composition, a composition of higher pH than the first composition, and mixtures thereof. The second composition may comprise any of the ingredients above-mentioned. The second composition aims at altering the treatment profile, particularly the hair colouring and/or bleaching profile, of the first composition. In other words, after mixing the second portion of the first composition with the second composition, the obtained mixed composition would treat hair in a different degree. For example, when providing and applying some of the first oxidative hair colouring and/or bleaching composition onto hair roots, and when mixing the remaining first composition with a dilutant composition and applying the resulting composition onto hair lengths and tips, the lengths and tips would be coloured and/or bleached in a less degree (i.e. lighter shade) than the hair roots, which would match the difference of colouration prior-treatment between the hair roots (virgin) and the hair lengths and tips (previously coloured and/or damaged hair).

The second composition may have a viscosity of from about 20 to about 200 Pa at 10 $s^{-1}$, or from about 20 to about 180 Pa at 10 $s^{-1}$, or from about 40 to about 180 Pa at 10 $s^{-1}$, from about 70 to about 170 Pa at 10 $s^{-1}$, as measured according to the viscosity test method The dilutant composition may comprise water and optionally at least one active component. The active component may be selected from the group consisting of surfactants, polymers, conditioning actives, solvents, C6 to C30 fatty alcohols, thickeners and mixtures thereof. The dilutant component may comprise up to 99%, or up to 90%, or up to 85% by weight of water; and/or it may comprise up to 25%, or from 1% to 20%, or from 5% to 20% by weight of the active component.

The second composition of lower pH than the first composition may comprise a pH reducing agent. A pH reducing agent is typically an acid which is added to a composition to lower the pH of the composition. The difference of pH between the first composition and the second composition may be at least 0.1 or at least 0.25 or at least 0.5 or at least 1. For example, the pH reducing agent may be selected from the group consisting of citric acid, phosphoric acid, salicylic acid, etidronic acid, acetic acid, ascorbic acid, hydrochloric acid, sulfuric acid and mixtures thereof.

The second composition of higher pH than the first composition may comprise a pH increasing agent. A pH increasing agent is typically a base which is added to a composition to increase the pH of the composition. The difference of pH between the second composition and the first composition may be at least 0.1 or at least 0.25 or at least 0.5 or at least 1. For example, the pH increasing agent may be selected from the group consisting of ammonia, ammonium bicarbonate, ammonium carbonate, ammonium chloride, ammonium hydroxide, ammonium phosphate, calcium carbonate, calcium hydroxide, calcium oxide, diammonium phosphate, dipotassium phosphate, ethanolamine, isopropanolamine, isopropylamine, magnesium hydroxide, magnesium oxide, potassium borate, potassium carbonate, potassium citrate, potassium hydroxide, potassium oxide, sodium bicarbonate, sodium borate, sodium carbonate, sodium hydroxide, sodium sesquicarbonate, sodium silicate, urea and mixtures thereof.

The Recipient 1

The method also comprises the step of providing a recipient 1 (step iii). The recipient 1 comprises a base 11, a frame 12 attached circumferentially to the base 11, and a cavity delimitated by the base 11 and the frame 12 and being suitable for containing a hair treatment composition, wherein the frame 12 comprises a partition means and/or indicia 13 for physically or virtually splitting the volume of the cavity into at least two adjacent sub-volumes. The recipient may also comprise a grasp hold 14 attached to the frame. The partition indicia 13 may be a substantially vertical line located on the frame 12 of the recipient 1, and optionally on its base 11, said line being engraved into and/or embossed onto the internal side of the frame 12. The partition means 13 may be a substantially vertical partition wall releasably and sealably attached to the internal side of the frame and/or the base of recipient, to split the volume of cavity into at least two adjacent, individualized sub-volumes (embodiment not shown in figures). The partition means may be attached to the recipient, after pouring the first composition and before applying a first portion of it to the hair; and/or wherein the partition wall may be detached from the recipient after retaining the second portion of the first composition.

One sub-volume of the cavity represents from about 90% to about 10%, preferably from about 80% to about 50%, more preferably from about 75% to about 55%, of the total volume of the cavity; and wherein the other sub-volume of the cavity inversely represents from about 10% to about 90%, preferably from about 50% to about 80%, more preferably from about 55% to about 75%, of the total volume of the cavity. Both sub-volume are adjacent as per an horizontal plan.

The base 11 of the recipient 1 may have a shape selected from circular, oval, squared, rectangular; alternatively a shape selected from circular, oval; alternatively a shape being circular. The longest distance of the base 11, between two diametrically opposed edge points, may range from about 120 mm and about 216 mm, or from about 145 mm to about 187 mm. The shortest distance of the base 11, between two diametrically opposed edge points, may range from about 30 mm to about 130 mm, or from about 55 mm to about 105 mm.

The frame 12 of the recipient 1 may have an average height ranging of from about 23 mm and about 80 mm, or from about 30 mm to about 55 mm.

The cavity may have a volume of from about 82 $cm^3$ to about 2246 $cm^3$, preferably from about 140 $cm^3$ to about 1300 $cm^3$, or from about 200 $cm^3$ to about 400 $cm^3$.

The recipient 1 may be made of a material being plastics; or is made of a material selected from PET, PETG, PP, PS, HDPE, plastic laminate papers, and mixtures thereof; or is made of a material selected from PET.

In a preferred embodiment, and as shown in FIGS. 1 to 5, the recipient 1 is a bowl, said recipient 1 has a base 11 of oval shape with the longest and the shortest distances of the base 11 between two diametrically opposed edge points being respectively about 157.2 mm and about 88.3 mm; a frame 12 having an average height of 41 mm; a cavity having a volume of about 290 $cm^3$; a partition means 13 being a substantially vertical, linear, embossed line located on the internal side of the frame and the corresponding linear, embossed line located on the internal side, wherein said partition means 13 defined one sub-volume of the cavity being about 42.2 $cm^3$; and wherein said recipient 1 is made of polyethylene tetraphtalate (PET).

The Mixing and/or the Application Tool 2

Figure 5:
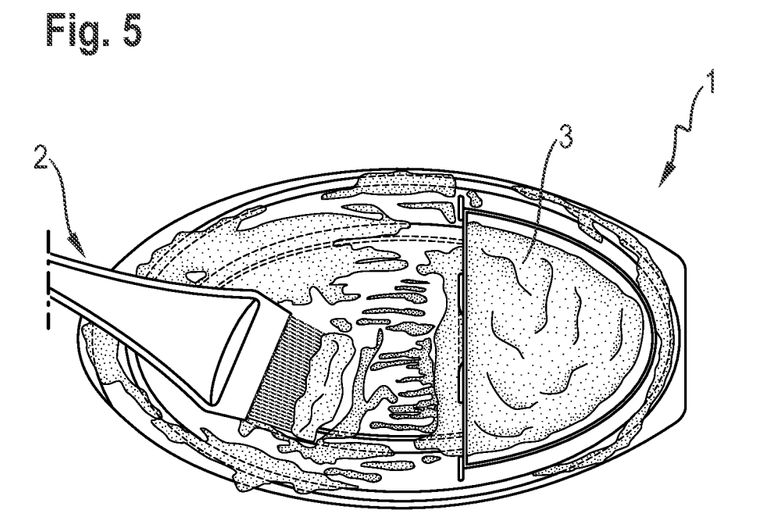
FIG. 5 is a top view of the recipient, when used together with a mixing and/or application tool at step viii) of the method.

The method may also comprise the step of providing a mixing and/or application tool 2 (step iv). Any suitable mixing and/or application tool known in the art may be used. In a preferred embodiment, as shown in FIG. 5, said tool 2 is a brush.

Application Steps

The method also comprises further steps.

The first composition is poured into the cavity of the recipient 1 (step v), then a first portion of the first composition is applied onto the hair (step vi). This first portion is preferably applied onto the hair roots. It may be applied using the application tool 2 abovementioned.

The applied first composition may be left onto hair, for a time sufficient for treating hair, preferably from about 1 min to about 60 min, or from about 10 min to about 40 min, or from about 15 min to about 30 min, or for about 20 min (step vii).

The second portion 3 of the non-applied first composition may be kept/retained, the volume of said second portion 3 corresponding to one of the two sub-volumes of the cavity (step viii). Whenever necessary, any excess of the second portion 3 may be eliminated. By excess, it is meant any amount exceeding said one sub-volume of the cavity.

The second composition is poured into the other sub-volume (step ix). The second composition is then mixed with the non-applied first composition 3 (step x). The mixing may be carried out using the application tool 2 abovementioned. These steps ix) and x) may be performed immediately after step vi, and/or concomitantly to step vii. The first composition and the second compositions may be mixed at a ratio of from about 1:2 to about 4:1, or from about 1:2 to about 2:1, or from about 2:1; alternatively at a ratio of less than about 1:2, or from about 1:25 to about 1:2.1, or from about 1:20 to about 1:2.1, or from about 1:10 to about 1:2.1, or from about 1:5 to about 1:2.1.

The mixed composition obtained in step (x) is subsequently applied onto hair (step xi). It is preferably applied onto the hair lengths and tips. It may be applied using the application tool 2 abovementioned.

The mixed composition may be left onto hair for a time sufficient for treating hair, preferably from about 1 min to about 60 min, or about from 1 min to about 40 min, or from about 5 min to about 20 min, or about 10 min (step xii).

The hair may be rinsed and/or cleaned (step xiii). Hair may be rinsed with an aqueous media, preferably with water, more preferably with tap water. Hair may be cleansed with a cleansing composition, preferably with a shampoo composition. Any suitable aqueous media and/or cleansing composition known in the art may be used. Hair roots on one hand and hair lengths and tips on the other hand may be rinsed and/or cleansed simultaneously or separately. When simultaneously, hair roots, lengths and tips may be rinsed and/or cleansed after the respective composition have been applied onto hair (steps vi and xi), and optionally after said compositions have been left on hair for a time sufficient for treating hair (steps vii and xii). When separately, hair roots may be rinsed and/or cleansed before applying the mixed composition onto the hair lengths and tips (steps xi).

A conditioning composition may be provided and applied onto hair. It may be applied instead of, before and/or after rinsing/cleansing hair (step xiv). Any suitable conditioning composition known in the art may be used.

A colour-refresher composition may be provided and applied onto hair. Any suitable colour-refresher composition known in the art may be used (step xv).

Hair may be dried (step xvi). Hair may be dried partially or completely, using a drying tool, for example a towel or an electrical drying tool such as a blow drier.

In another aspect, the present invention relates to a hair treatment kit. The kit is suitable for extemporaneous preparation of hair treatment compositions as defined hereinbefore. The kit comprises: a first composition having a viscosity of from about 20 to about 200 Pa at 10 $s^{-1}$, as measured according to the viscosity test method; a second composition, wherein said composition is compatible for mixing with the first composition; and a recipient 1 comprising a base 11, a frame 12 attached circumferentially to the base 11, optionally at least one grasp hold 14 attached to the frame 12, and a cavity delimitated by the base 11 and the frame 12 and being suitable for containing hair colouring compositions, wherein the frame 12 comprises a partition means and/or indicia 13 for virtually or physically splitting the volume of cavity into at least two adjacent sub-volumes. Said first composition, second composition and recipient 1 are defined hereinbefore. The kit may also comprise a rinsing and/or cleansing composition, preferably a shampoo composition; and/or a conditioning composition; and/or a colour-refresher composition. The kit may also comprise a mixing and/or application tool 2, preferably a brush. The rinsing and/or cleansing composition, the conditioning composition, the colour-refresher composition and the mixing and/or application tool are defined hereinbefore. The kit may also comprise a set of instructions comprising instructing the user to colour its hair according to the method defined hereinbefore. The instructions may be conveyed via a text description and/or using schematic representation and/or using a series of pictures, detailing the various steps to be carried out.

In another aspect, the present invention relates to a recipient 1 suitable for containing hair treatment compositions comprising: a base 11; a frame 12 attached circumferentially to the base 11; and a cavity delimitated by the base 11 and the frame 12 and being suitable for containing hair treatment compositions, wherein the frame 12 comprises a partition means and/or indicia 13 for virtually or physically splitting the volume of cavity into at least two adjacent sub-volumes. The recipient 1 may also comprise a grasp hold 14 attached to the frame. The recipient 1 is further defined hereinbefore.

The inventors have surprisingly found that the provision of such a recipient 1, comprising partition means and/or indicia 13, allows the user such as the non-trained consumer to put into practice the method of treating hair, using two differing compositions to be applied on different portions of hair such as on hair roots and on lengths/tips, in an easy and intuitive fashion. This recipient allows accomplishing a hair treatment method in a fashion unmet so far.

In another aspect, the present invention relates to the use of a recipient as defined hereinbefore, as a support for containing two differing hair treatment compositions, before their application onto different portions of hair, preferably before their respective application on the roots and lengths/tips of hair.

The viscosity of a composition is measured using a TA Instruments AR 2000 Rheometer or equivalent device equipped with a Peltier plate and a 6 cm flat acrylic plate with cross hatchings. The instrument is calibrated according to the manufacturer's instructions and the Peltier plate is set at 25.0° C. The cone is raised to a position approximately 4.5 cm above the plate. Immediately after the mixing, approximately 10 g of the mixture is transferred gently onto the centre of the Peltier plate using a spatula. The cone is lowered to obtain the specified gap between the tip of the cone and the upper surface of the Peltier plate. The gap setting is specified by the manufacturer of the cone and is typically approximately 1000 microns. The rheometer is programmed to operate in rotational mode with the shear stress ramped from 0.1 to 600 Pa over a period of 4 minutes, termination at 1000 reciprocal seconds. Rotation is initiated immediately after the specified gap is established. Viscosity data collected during the measurement period are shear stress (Pa) plotted as a function of shear rate ($s^{-1}$).

EXAMPLES

Dye component formulations: Each of the formulations (100% total) detailed below comprises a generic base and a specific dye mix. The base comprises the following compounds (by total weight of dye component): 9.0% Crodafos CES (cetearyl alcohol, dicetyl phosphate, ceteh-10 phosphate); 2.0% cetearyl alcohol; 1.0% steareth-200; 7.5% propylenglycol; 0.1% EDTA disodium salt; 0.3% ascorbic acid; 0.4% sodium sulphite; 1.0% ammonium sulfate and/or sodium sulfate; 3.35% Na3-ethenediamine disuccinate; 0.25% perfume. The dye mixes comprise the following compounds (by total weight of dye component):

| Shades | 6/0 | 5/0 | 7/0 | 9/0 | 10/0 | 7/7 | 5/43 |
|---|---|---|---|---|---|---|---|
| Toluene-2,5-diamine Sulfate | 0.935 | 1.309 | 0.69 | 0.182 | | 0.7 | 1.4 |
| 4-Amino phenol | 0.115 | 0.161 | 0.083 | 0.066 | | | 0.58 |
| Resorcinol | 0.455 | 0.637 | 0.337 | 0.11 | | 0.165 | 0.88 |
| 2-Methyl-recorcinol | | | | | | 0.165 | |
| 2.4-Diamino-phenoxy-ethanol HCL | 0.018 | 0.025 | 0.01 | | | | |
| m-Amminophenol | 0.105 | 0.145 | 0.074 | 0.045 | | 0.013 | 0.185 |
| 2-Methyl-5-hydroxy-ethylamino-phenol (Paox) | 0.025 | 0.035 | 0.02 | 0.003 | | 0.039 | 0.34 |
| 2-Amino-6-chloro-4-nitrophenol | | | | | | 0.008 | |
| Ammonium Hydroxide 25% | 0.743 | 1.04 | 0.546 | 0.163 | | 0.51 | 1.28 |
| Ammonia 25% of buffer | | | | 0.48 | 0.48 | | |
| Ammonium Hydroxide 25% | 6.37 | 4 | 7.28 | 7.69 | 5.5 | 4.5 | 4.5 |
| Water | qsp | qsp | qsp | qsp | qsp | qsp | qsp |

Developer Component Formulations

| Developer component | 1 | 2 | 3 | 4 |
|---|---|---|---|---|
| Water Purified | | | | |
| Disodium EDTA. | 0.04 | 0.04 | | |
| Etidronic Acid | 0.08 | 0.08 | 0.01 | 0.01 |
| Aculyn 33 | 9.00 | 9.00 | | |
| Acrylates Steeareth-20 methacrylate copolymer | 0.10 | 0.10 | | |
| Hydrogen peroxide solution, 50% | 12.00 | 18.00 | 12.00 | 18.00 |
| Simethicone Emulsion | 0.01 | 0.01 | | |
| Cetearyl alcohol | | | 3.4 | 3.4 |
| Ceteareth-25 | | | 0.8 | 0.8 |
| Salicyclic acid | | | 0.1 | 0.1 |
| Disodium phosphate | | | 0.08 | 0.08 |

Dilutant composition 1: 1.8% Propylene glycol, 1.5% Hydroxycellulose, 2.0% Quaternium-80 (in 50% glycol), 1.25% Soytrimmonium chloride (60%), 0.5% PEG-40 hydrogenated castor oil, 0.4% Phenoxyethanol, 0.7% Cocoamidopropyl betaine, 0.002% Formic acid, 0.2% Perfume, 0.3% DMDM hydantoin, 0.1% Hydrolised sweet almond protein, 0.1% Disodium EDTA and up to 100% water, by total weight of the dilutant composition.

Dilutant component 2: 0.1% Guar hydroxypropyltrimonium chloride, 4.0% Cetrimonium chloride, 0.4% Phenoxyethanol, 0.3% Methyl paraben, 0.05% Titanium dioxide, 4.0% Cetearyl alcohol, 0.5% Fragrance, 0.1% Fruit extract and up to 100% water, by total weight of the dilutant composition.

Dilutant component 3: 2.0% Stearamidopropyl dimethylamine, 2.5% Cetyl alcohol, 4.5% Stearyl alcohol, 0.1% Ethylene diamine tetra acetic acid EDTA, 0.4333% Preservatives, 4.995% Amodimethicone, 0.005% Trimethylsiloxysilicate MQ resin, 0.64% L_Glutamic acid, 0.2250% Panthenyl ethyl ether, 0.045% Panthenol, 0.05% Safflower, 0.05% Coconut oil, 0.1% Hydrolyzed sweet almond, 0.005% Aloe Gel, 0.4% perfume and up to 100% water, by total weight of the dilutant composition.

Recipient 1: a base 11 of oval shape with the longest and the shortest distances of the base 11 between two diametrically opposed edge points being respectively 157.2 mm and 88.3 mm; a frame 12 having an average height of 41 mm; a cavity having a volume of 290 cm$^3$; a partition means 13 being a substantially vertical, linear, embossed line located on the internal side of the frame 12 and the corresponding linear, embossed line located on the internal side, wherein said partition means 13 defined one sub-volume of the cavity being 42.2 cm$^3$; material being PET.

Figure 1:
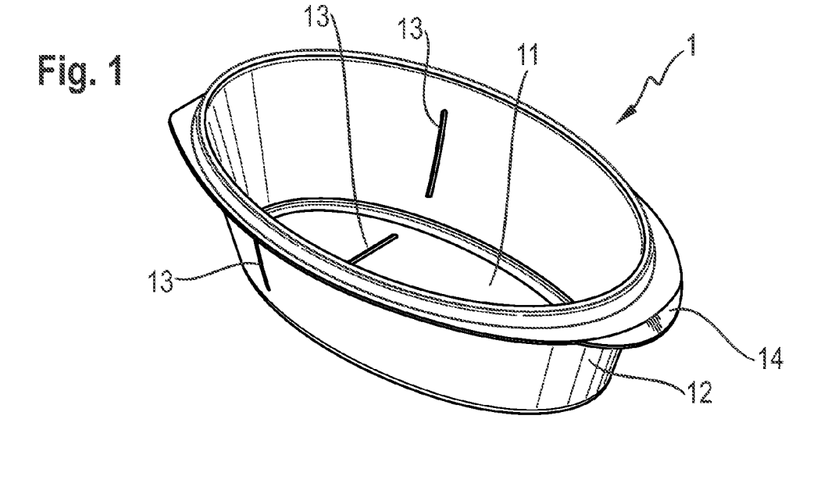
FIG. 1 is a perspective view of the recipient.
Figure 2:
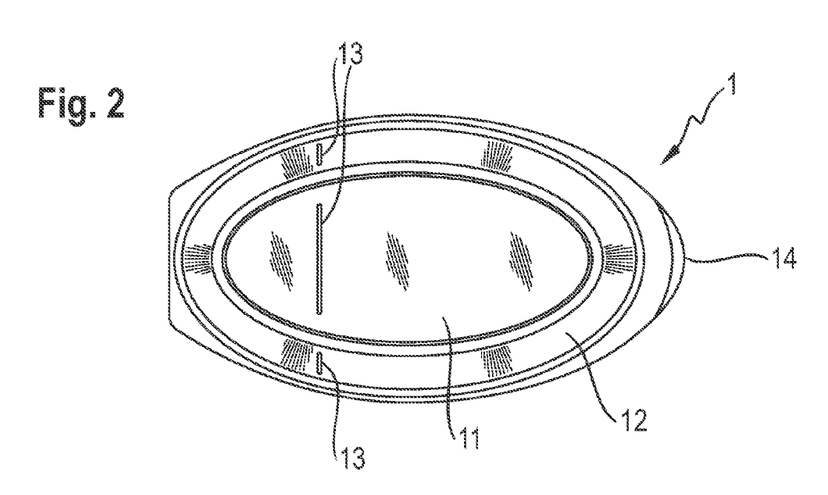
FIG. 2 is a top view of the recipient.
Figure 3:
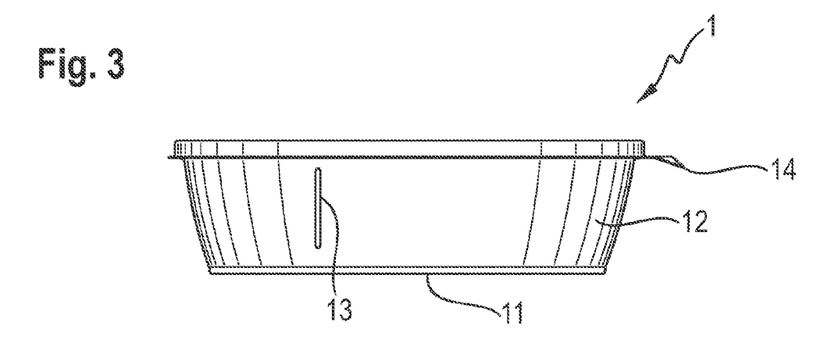
FIG. 3 is a front view of the recipient.
Figure 4:
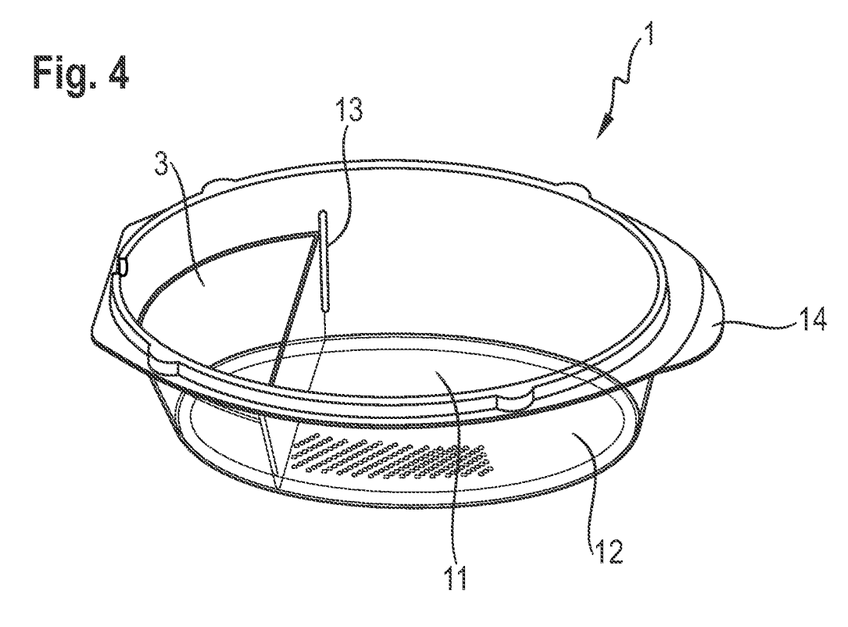
FIG. 4 is a perspective view of the recipient, computer-simulating step viii) of the method for treating hair.

Method of treating hair: It is a provided to a non-trained user (i.e. a consumer, not a professionally trained hair dresser) a recipient as shown in the FIGS. 1 to 5. The first composition is provided by pouring 60 mL of a dye component and 60 mL of a developer component into the recipient, and then homogeneously mixing both components (ratio 1:1) using a conventional brush 2 as shown in FIG. 5. Between 55% and 75% of the first composition (aka the first portion of the first composition) is applied onto the hair roots, using the brush 2. Said applied first composition is left onto hair root for a time sufficient for colouring and/or bleaching hair i.e. for about 20 min. Meanwhile, the non-applied portion 3 of the first composition (aka the second portion of the first composition) is kept and, whenever necessary, pushed and/or packed in the smallest sub-volume of the cavity, which is virtually delimitated by the partition lines embossed onto the internal sides of the frame 12 and the base 11, as shown in FIG. 4 (computer simulation) and in FIG. 5 (recipient upon use). The dilutant composition (aka the second composition) is then poured into the other sub-volume of the cavity. The second portion 3 of the first composition and the second composition are mixed homogeneously using the brush 2. The mixed composition is then applied onto the hair lengths and tips, using the brush 2. Said applied mixed composition is left onto hair root for a time sufficient for colouring and/or bleaching hair i.e. for about 10 min. The waiting time for the applied first composition and the applied mixed composition, i.e. respectively about 20 min and about 10 min, elapse preferably at the same time. Hairs are then rinsed abundantly using running water, for removing the composition. Whenever necessary, the hair are cleansed using a conventional shampoo composition, the hair are treated using a condition composition and/or a colour-refresher composition and/or the hair are dried using a towel or a blow drier. A superior hair colouring and/or bleaching performance, particularly a superior root to tip treatment evenness, is obtained.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A method for treating hair comprising the steps of:
   i) providing a first composition having a viscosity of from about 20 to about 200 Pa at 10 s$^{-1}$;
   ii) providing a second composition, wherein said composition is compatible for mixing with the first composition;
   iii) providing a recipient comprising a base, a frame attached circumferentially to the base, at least one grasp hold attached to the frame, and a cavity delimitated by the base and the frame and being suitable for containing a hair treatment composition, wherein the frame comprises a partition means and/or indicia for physically or virtually splitting the volume of the cavity into at least two adjacent sub-volumes;
   iv) providing a mixing and/or application tool;
   v) pouring the first composition into the cavity of the recipient;
   vi) applying a first portion of the first composition onto the hair;
   vii) leaving the applied first composition onto hair, for a time sufficient for treating hair;
   viii) retaining a second portion of the non-applied first composition, the volume of said second portion corresponding to one of the two sub-volumes of the cavity;
   ix) pouring the second composition into the other sub-volume;
   x) mixing the second composition with the non-applied first composition;
   xi) applying the mixed composition obtained in step x) to the hair;
   xii) leaving the mixed composition onto hair for a time sufficient for treating hair; and
   xiii) rinsing and/or cleansing hair.
2. The method according to claim 1, wherein the first portion of the first composition is applied in step vi) to the hair roots and the mixed composition obtained in step x) is applied in step xi) to the hair lengths and tips.

3. The method according to claim 1, wherein the applied first composition is left onto hair in step vii) from about 1 min to about 60 min and the mixed composition is left onto hair in step xii) from about 1min to about 60 min.

4. The method according to claim 1, wherein the first composition is selected from the group consisting of a hair colouring and/or bleaching hair, a hair perming composition, and mixtures thereof; or a hair colouring and/or bleaching composition; or a hair colouring composition comprising a dye compound; or a hair colouring composition comprising a dye compound selected from the group consisting of an oxidative dye precursor, a direct dye compound, and mixtures thereof; or an oxidative hair colouring composition comprising an oxidative dye precursor and a direct dye compound.

5. The method according to claim 1, wherein the first composition is an oxidative hair colouring composition which is obtained by:
providing a developer component comprising an oxidizing agent;
providing a dye component comprising an oxidative dye precursor and/or an alkalizing agent;
pouring, sequentially or simultaneously, the developer and the dye components into the cavity of the recipient;
mixing the developer component and the dye component homogenously.

6. The method according to claim 5, wherein the developer component and the dye component are mixed homogeneously at a mixing ratio of from about 1:5 to about 5:1.

7. The method according to claim 1, wherein the second composition is selected from the group consisting of a hair colouring and/or bleaching composition, a hair perming composition, a dilutant composition, a composition of lower pH than the first composition, a composition of higher pH than the first composition, and mixtures thereof.

8. The method according to claim 1, wherein the first composition and the second composition are mixed at a ratio of from about 1:2 to about 4:1.

9. The method according to claim 1, wherein the steps vi), x) and/or xi) are carried out using the tool provided in step iv).

10. The method according to claim 1, wherein the partition indicia is a substantially vertical line located on the frame of the recipient, said line being engraved into and/or embossed onto the internal side of the frame.

11. The method according to claim 1, wherein the partition means is a substantially vertical partition wall releasably and sealably attached to the internal side of the frame and/or the base of recipient, to split the volume of cavity into at least two adjacent, individualized sub-volumes.

12. The method according to claim 1, wherein the partition means is attached to the recipient, after pouring the first composition and before applying a first portion of it to the hair; and/or wherein the partition wall is detached from the recipient after retaining the second portion of the first composition.

13. The method according to claim 1, wherein one sub-volume of the cavity represents from about 90% to about 10% of the total volume of the cavity.

14. The method according to claim 1, wherein one sub-volume of the cavity represents from about 80% to about 50% of the total volume of the cavity.

15. The method according to claim 1, wherein one sub-volume of the cavity represents from about 75% to about 55% of the total volume of the cavity.

16. The method according to claim 1, wherein:
the base of the recipient has a shape selected from circular, oval, squared, rectangular; alternatively a shape selected from circular, oval; alternatively a shape being circular; and/or
the base has the longest distance between two diametrically opposed edge points ranging of from about 120 mm and about 216 mm; and the shortest distance between two diametrically opposed edge points ranging of about 30 mm to about 130 mm; and/or
the frame of the recipient has an average height ranging of from about 23 mm and about 80 mm; and/or,
the cavity has a volume of from about 82 $cm^3$ to about 2246 $cm^3$.

17. The method according to claim 16, wherein the cavity has a volume of from about 140 $cm^3$ to about 1300 $cm^3$.

18. The method according to claim 1, wherein the recipient is made of a material being plastics; or is made of a material selected from PET, PETG, PP, PS, HDPE, plastic laminate papers, and mixtures thereof; or is made of a material selected from PET.

\* \* \* \* \*